(12) United States Patent
Weiss (10) Patent No.: US 10,960,495 B2
(45) Date of Patent: Mar. 30, 2021

(54) LASER CURTAIN CONTAINMENT SYSTEM

(71) Applicant: George Weiss, Cold Spring, NY (US)

(72) Inventor: George Weiss, Cold Spring, NY (US)

( * ) Notice: Subject to any disclaimer, the term of this patent is extended or adjusted under 35 U.S.C. 154(b) by 434 days.

(21) Appl. No.: 16/019,476

(22) Filed: Jun. 26, 2018

(65) Prior Publication Data

US 2018/0369965 A1    Dec. 27, 2018

Related U.S. Application Data

(60) Provisional application No. 62/524,949, filed on Jun. 26, 2017.

(51) Int. Cl.
| | |
|---|---|
| *E06B 9/42* | (2006.01) |
| *B23K 26/70* | (2014.01) |
| *E06B 9/90* | (2006.01) |
| *F16P 1/06* | (2006.01) |
| *B23K 37/00* | (2006.01) |
| *A61B 90/00* | (2016.01) |

(52) U.S. Cl.
CPC ............ *B23K 26/706* (2015.10); *A61B 90/04* (2016.02); *B23K 37/006* (2013.01); *E06B 9/42* (2013.01); *E06B 9/90* (2013.01); *F16P 1/06* (2013.01)

(58) Field of Classification Search
CPC ..... E06B 9/40; E06B 9/42; E06B 9/78; E06B 2009/785; E06B 2009/405; E06B 9/11; E06B 9/54; E06B 9/13; E06B 9/17; E06B 9/17007; E06B 9/17015; E06B 9/17023; E06B 9/1703; E06B 9/171; E06B 9/50; E06B 2009/2425; B23K 26/706; B23K 37/006; F16P 1/06; A47H 1/13; A47H 23/00; A47H 21/00
See application file for complete search history.

(56) References Cited

U.S. PATENT DOCUMENTS

| | | |
|---|---|---|
| 4,901,738 A | 2/1990 | Brink et al. |
| 6,685,592 B2 | 2/2004 | Fraczek et al. |

(Continued)

OTHER PUBLICATIONS

Thor Labs LPC13, available Feb. 13, 2018 access Oct. 27, 2020 from , https://www.thorlabs.de/catalogpages/obsolete/2018/LPC13. pdf (Year: 2018).*

(Continued)

*Primary Examiner* — Daniel P Cahn
*Assistant Examiner* — Jeremy C Ramsey
(74) *Attorney, Agent, or Firm* — Law Office of Leo Zucker (57) ABSTRACT

A laser containment system in which a platform is suspended above a table on which laser light experiments will be performed. A number of curtain pockets having U-shaped cross sections are mounted beneath the platform, with the pocket openings facing down toward the sides of the table. A roller is mounted between end walls inside each pocket, and a laser curtain long enough to be lowered past a corresponding side of the table is wound on each roller. A clutch supported on an end wall of each pocket operatively engages an end of the roller inside the pocket to lower or raise the curtain on the roller. An associated clutch pulley is disposed outside the end wall of each pocket on which the clutch is supported. A curtain chain engages the circumference of the pulley, and the chain hangs outside the curtain when lowered for access by a user.

8 Claims, 9 Drawing Sheets

(56) References Cited

U.S. PATENT DOCUMENTS

| | | | |
|---|---|---|---|
| 7,626,763 B2 | 12/2009 | Harrison et al. | |
| 8,672,115 B1 | 3/2014 | Jennings et al. | |
| 9,790,737 B2 | 10/2017 | Seib | |
| 2011/0061817 A1* | 3/2011 | Smith | E06B 9/54 160/121.1 |
| 2013/0240661 A1* | 9/2013 | Wills | E06B 9/42 242/615 |
| 2017/0211315 A1* | 7/2017 | Fleischman | E04B 1/0046 |
| 2017/0328129 A1* | 11/2017 | Maertens | E06B 9/58 |

OTHER PUBLICATIONS

Laservision USA, Laser Safety Barriers, online advertisement (2 pages), undated.
Newport Corporation, Laser Safety Curtains, online advertisement (2 pages), undated.
Curtain Ninja, Acmeda RB09 45mm Easy-Lock Chain Clutch End, online advertisement (4 pages), undated.

* cited by examiner

FIG. 1 (Known Art)

FIG. 2 (Known Art)

LASER CURTAIN CONTAINMENT SYSTEM

CROSS REFERENCE TO RELATED APPLICATION

This application claims priority under 35 U.S.C. § 119(e) based on U.S. Provisional Patent Application No. 62/524,949 filed Jun. 26, 2017, the entire contents of which are incorporated by reference.

BACKGROUND OF THE INVENTION

Field of the Invention

The present invention relates to curtains made to absorb laser radiation, and particularly to systems that employ such curtains to contain radiation from laser sources used in experiments at research facilities.

Discussion of the Known Art

Researchers in medical and scientific laboratories often use sources of laser light in the course of their work. The radiation from such sources can injure persons and damage property nearby if not properly contained. Fabrics capable of shielding persons from harmful laser radiation are known and commercially available. See, e.g., U.S. Pat. No. 4,901,738 (Feb. 20, 1990) and U.S. Pat. No. 7,626,763 (Dec. 1, 2009), both of which are incorporated by reference. The fabrics are used, for example, in containment systems that prevent light from radiating beyond laboratory tables on which laser experiments are triggered from a safe distance by workers or students.

Original laser containment systems were large and unwieldy, and consumed expensive floor space considering many users are non-profit research labs in major cities where rents are high. As containment systems evolved and demand increased, contractors began to wind laser absorbing or shielding curtains on window shade rollers, and to install the rollers together with chain-operated clutches above the sides of the tables. Such clutches are disclosed, for example, in U.S. Pat. No. 6,685,592 (Feb. 3, 2004), and U.S. Pat. No. 9,790,737 (Oct. 17, 2017), both of which are incorporated by reference.

Problems arose, however, because in order to allow users to lower the laser curtains while standing next to a lab table, the rollers and clutches were installed so that the curtains unwound from the back of the rollers, i.e., the side of the rollers that faced away from the table. Thus, when lowered, the curtains were spaced from the sides of the table by an amount corresponding to the depths of the assembled rollers and clutches. Because of this, the side edges of the lowered curtains were also spaced apart from one another at each corner of the table, making it necessary to provide separate absorbing flaps to bridge the space between the edges of the curtains at the table corners. Moreover, because the chains for lowering and raising the curtains hung on the sides of the absorbing flaps that faced the table, the flaps also had to be separately handled and moved each time a user would access the chains from outside in order to raise the curtains.

As a result, early laser containment systems had the following disadvantages:

A. Potential safety hazards to both person and property if a user mistakenly believed an experiment had ended, and then reached through the lowered curtains from outside in order to pull the chains and raise the curtains.

B. When blindly reaching through the lowered curtains from outside, a user could unknowingly disturb an experiment then in progress on the table.

C. Since the curtains and corner flaps had to be moved out of the way each time a user reached into the contained field from outside, the curtain fabric was subject to becoming torn or damaged.

D. No known construction standard had been established for installing laser containment systems in research laboratories in a spatially efficient and cost effective manner.

Figure 1:
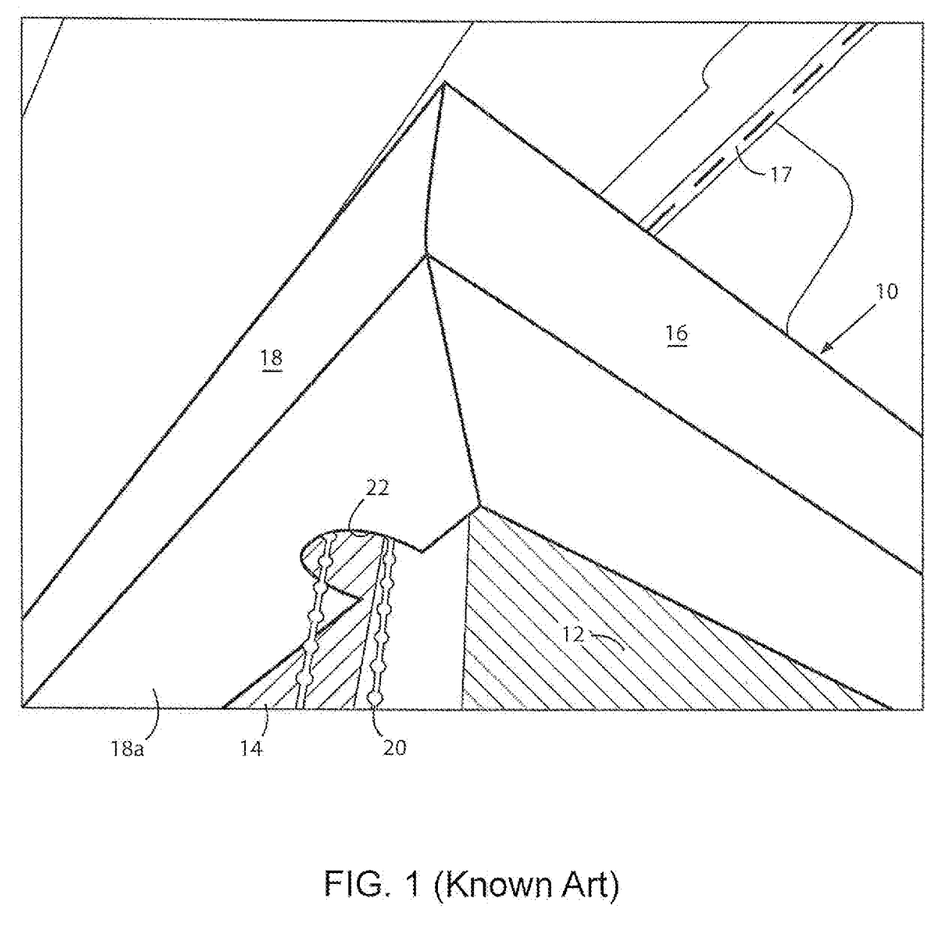
FIG. 1 is a perspective view of a corner of a known laser curtain containment system.
Figure 2:
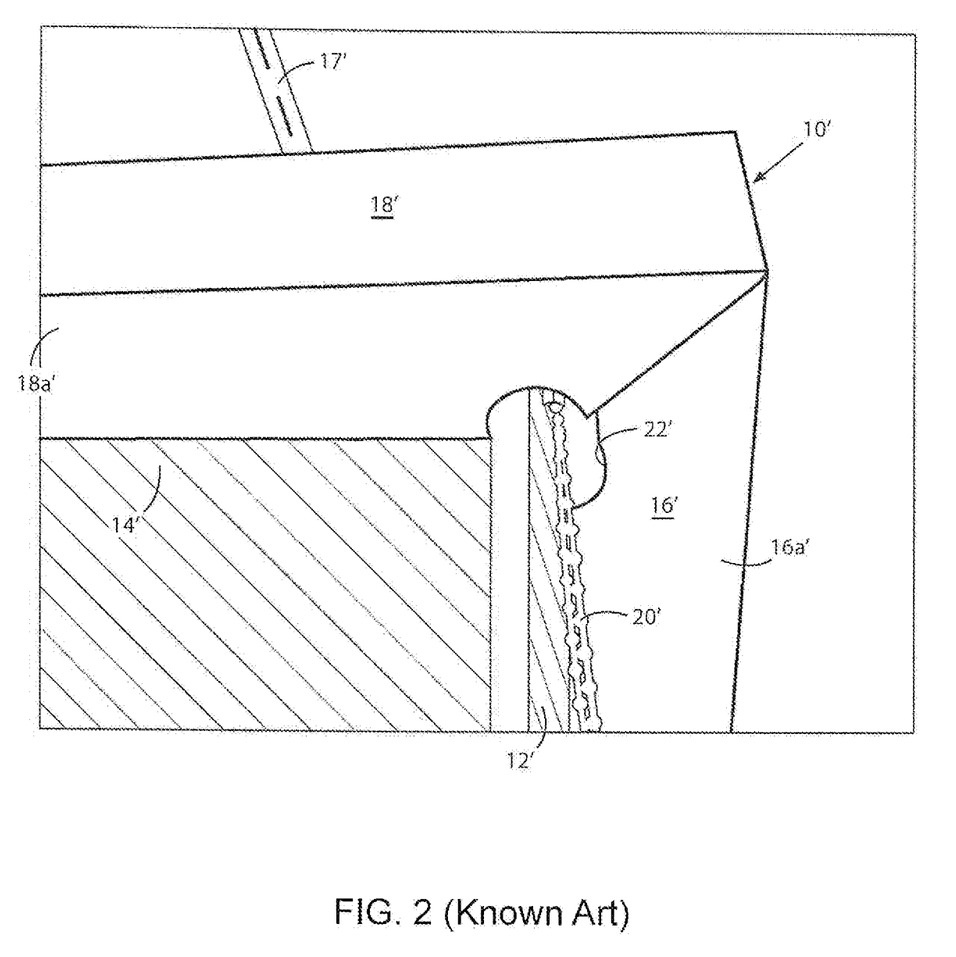
FIG. 2 is a perspective view of a corner of another known laser curtain containment system.

Attempts were made to install the curtain rollers and clutches so that the curtains would descend closer to the sides of the table, and to position the clutch chains so they could be operated outside of the lowered curtains. FIG. 1 shows a corner portion of one such containment system 10, and FIG. 2 shows a corner portion of a similar containment system 10'.

In FIG. 1, two laser curtains 12, 14 of the system 10 are arranged to be lowered past corresponding sides of a lab table below (not shown), from above a corner of the table. The curtains 12, 14 are wound on associated cylinders or rollers, wherein each roller is mounted inside a corresponding elongated metal pocket 16, 18. The pockets 16, 18 may be formed in a known manner, for example, by bending elongated metal sheets so that each pocket has a U-shaped cross section.

Each roller is driven for rotation about its axis by a conventional, chain-operated clutch that is also mounted inside each pocket and which engages an axial end of the roller. A chain 20 engages the circumference of a pulley on each clutch, and each clutch turns its associated roller to lower or raise the wound curtain depending on which length of the chain 20 is pulled from below by a user.

The upper side walls of the pockets 16, 18 are fastened to horizontal tracks 17 with the open sides of the pockets 16, 18 facing inward. The tracks 17 are fixed along a ceiling or elevated platform at the facility where the system 10 is deployed. As shown in FIG. 1, the axial ends of the installed pockets 16, 18 are brought flush with one another, and the pockets form a 90-degree angle to correspond with a corner of a lab table below.

The roller carrying curtain 14 is mounted in pocket 18 so that the curtain unwinds from the side of the roller facing the open side of the pocket 18. Likewise, the roller carrying curtain 12 is mounted in pocket 16 so that the curtain also unwinds from the side of the roller facing the open side of the pocket 16.

As seen in FIG. 1, a rounded cutout 22 is formed in the edge of a bottom wall 18a of pocket 18 so that both lengths of the beaded chain 20 hang unobstructed from the clutch mounted inside pocket 18 for user access below the pocket. Because both lengths of the chain 20 must move simultaneously into and out of the pocket 18 whenever the chain is used to lower or raise the curtain 14, it was found that the chain 20 had a tendency to bind up on the edge of the cutout 22 and produce noise.

Further, even though the curtains 12, 14 in FIG. 1 when lowered could approach the sides of a table below more closely than in prior systems, the side edges of the curtains were still spaced apart at the corners of the table. This is because in order to accommodate the clutches at the ends of the curtain rollers inside the pockets 16, 18, the width of the rolled curtains could not extend over the full length of the pockets. Thus, separate laser absorbing flaps were still required to prevent laser light from escaping between the side edges of the curtains at the table corners.

In FIG. 2, components of the illustrated system 10' that are similar to those in the system 10 in FIG. 1 are identified via the same reference numerals, followed by an apostrophe (').

In the system 10' in FIG. 2, two laser curtains 12', 14' are arranged to be lowered past corresponding sides of a lab table (not shown) adjacent to a corner of the table. The curtains 12', 14' are wound on associated rollers, and each roller is mounted inside a corresponding elongated metal pocket 16', 18'. The pockets 16', 18' may also be formed in a known manner, for example, by bending elongated metal sheets to define a U-shaped cross section for each pocket.

Each roller is engaged at an axial end by a clutch that is mounted together with the roller inside the corresponding pocket. A beaded chain 20' engages the circumference of a pulley on each clutch, and each clutch turns its associated roller to lower or raise the wound curtain depending on which length of the chain 20' is pulled from below by a user.

As seen in FIG. 2, a rounded cutout 22', larger than the cutout 22 in FIG. 1, is formed to extend into the lower edges of the adjoining bottom walls 16a', 18a' of pockets 16', 18', so that both lengths of the chain 20' hang unobstructed from the clutch mounted inside the pocket 18' for access below. Notwithstanding the larger size of the cutout 22', the chain 20' still had a tendency to bind on the edge of the cutout 22' and create noise whenever the chain was pulled to lower or raise the curtain 14' in pocket 18'. The adjoining ends of the pockets 16', 18' also had an unfinished appearance. Moreover, as in the system 10 in FIG. 1, the side edges of the curtains 12', 14' were still separated enough as to require the use of separate absorbing flaps at the corners of a table below.

SUMMARY OF THE INVENTION

According to the invention, a laser curtain containment system includes a platform or track suspended above a table on which a source of laser light can be activated. A number of elongated curtain pockets having a generally U-shaped cross section are mounted beneath the platform so that an open side of the pocket faces downward toward a corresponding side of the table.

An elongated roller is mounted for rotation between end walls inside each curtain pocket, and a laser curtain is wound on each roller. Each curtain is wide enough to extend over substantially the length of the roller between the end walls of the corresponding curtain pocket, and the curtain is sufficiently long to be lowered past a corresponding side of the table when unwound.

A clutch is supported on an end wall of each curtain pocket for operatively engaging an end of the roller inside the pocket to lower or raise the curtain wound on the roller. The clutch has an associated pulley disposed outside the end wall of the pocket on which the clutch is supported. A chain engages the circumference of the pulley, and the chain hangs outside the curtain for access by a user when the curtain is lowered.

For a better understanding of the invention, reference is made to the following description taken in conjunction with the accompanying drawing and the appended claims.

DETAILED DESCRIPTION OF THE INVENTION

Figure 3:
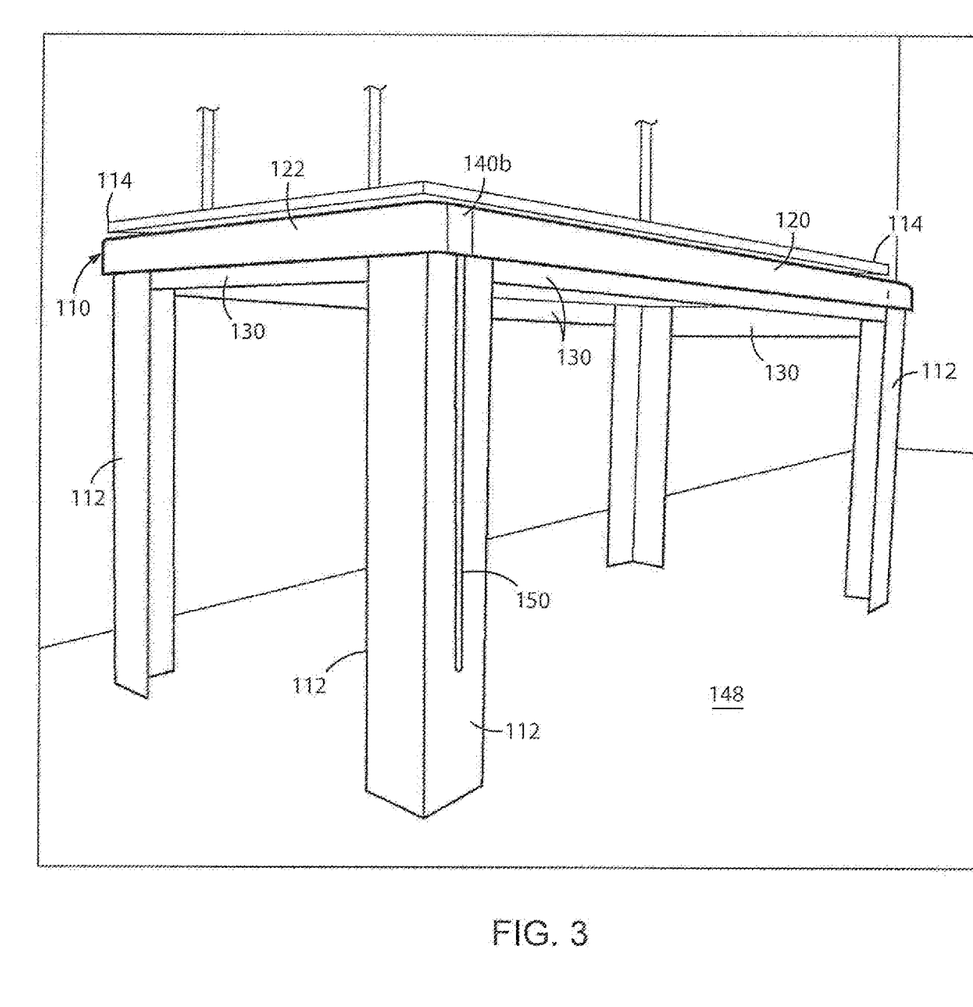
FIG. 3 is a perspective view of a laser curtain containment system according to the invention, installed above a laboratory floor.
Figure 4:
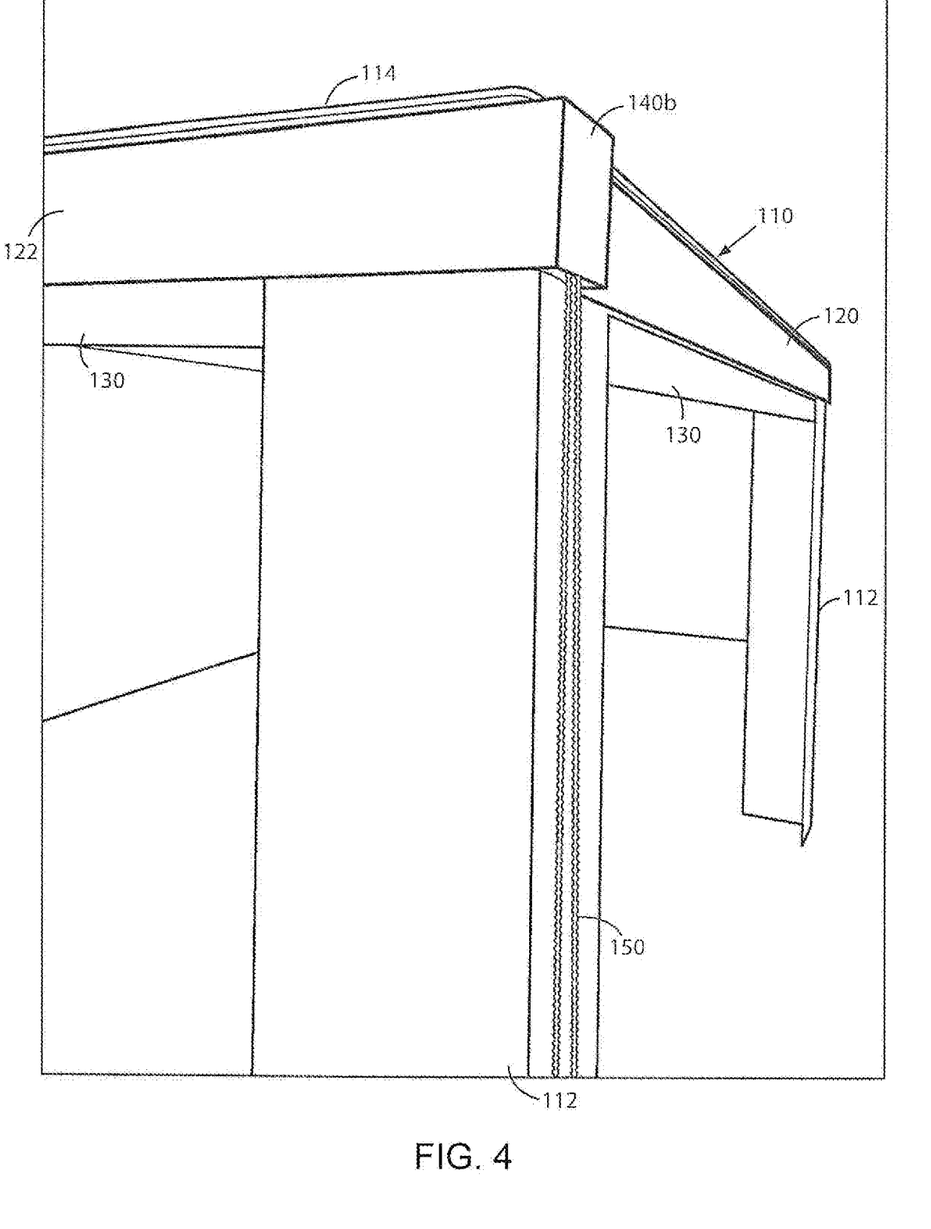
FIG. 4 is an enlarged perspective view of a front corner of the inventive system in FIG. 3.
Figure 5:
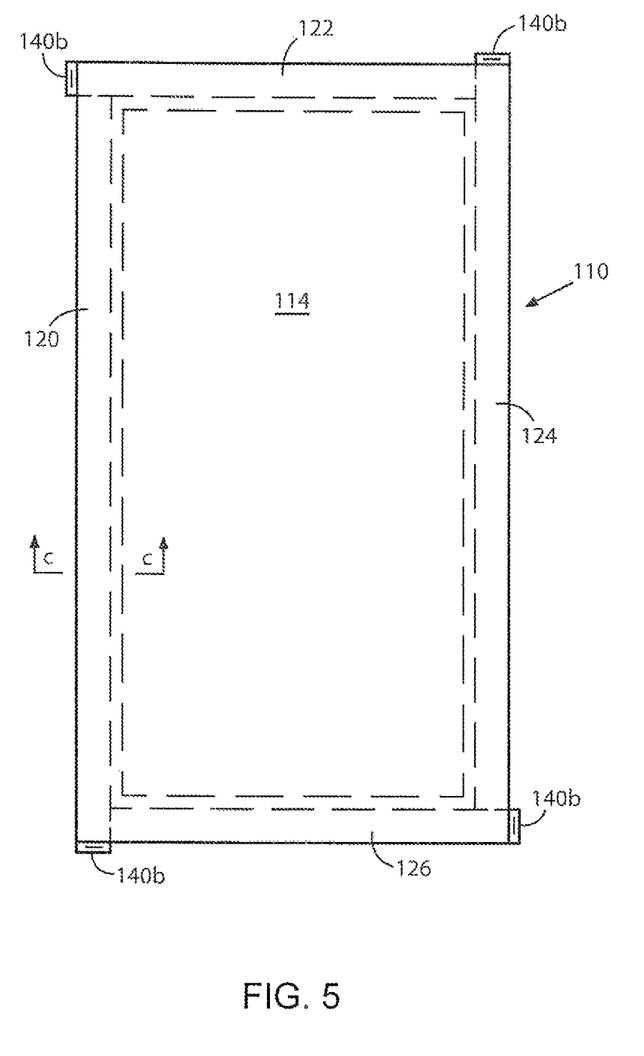
FIG. 5 is an overall top plan view of the inventive system.

FIG. 3 is a perspective view of a laser curtain containment system 110 according to the invention installed above a floor 148 at, e.g., a research facility or laboratory. The overall dimensions of the system 110 are scalable so that the system can accommodate and contain laser light within the bounds of a conventional laboratory table (not shown). FIG. 4 is an enlarged perspective view of adjoining curtain pockets 120, 122 of the system 110, including corner absorbing pieces 112 the tops of which may be fastened (e.g., via hook and loop material) to the adjoining pockets. FIG. 5 is a top plan view of the system 110.

In the installation in FIG. 3, the system 110 is fastened on a bottom surface of a flat rectangular platform 114 (see FIG. 5) that may measure, e.g., about 105 inches by about 57 inches depending on the dimensions of a table that will be located beneath the platform 114 for containment of laser radiation. As mentioned, since the platform 114 is typically installed over a laboratory table, the platform should also be able to support electrical wiring and other services (e.g., chemical liquids and gases) that may need to be routed to and from the table for use in experiments. As seen in FIG. 3, the platform 114 can be suspended securely from a ceiling at the facility where the system 110 is installed.

Figure 6:
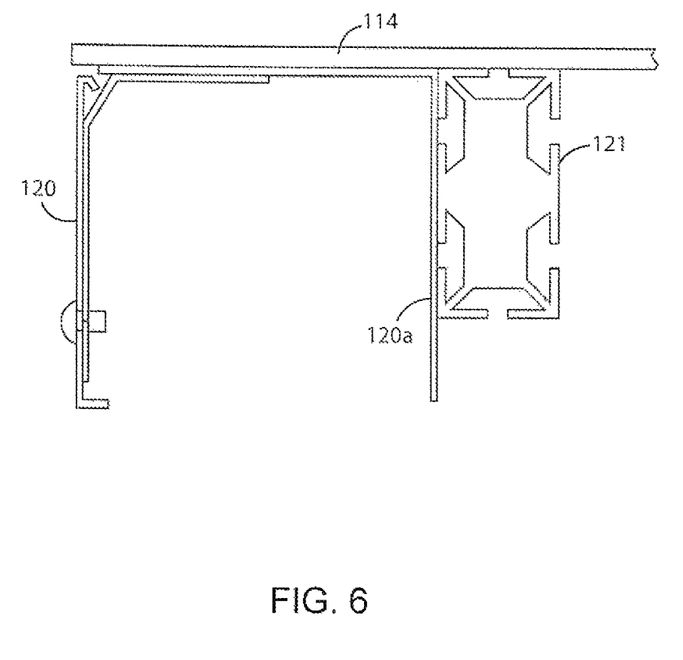
FIG. 6 is a cross-sectional view of a curtain pocket of the inventive system, as seen in elevation along line C-C in FIG. 5.
Figure 7:
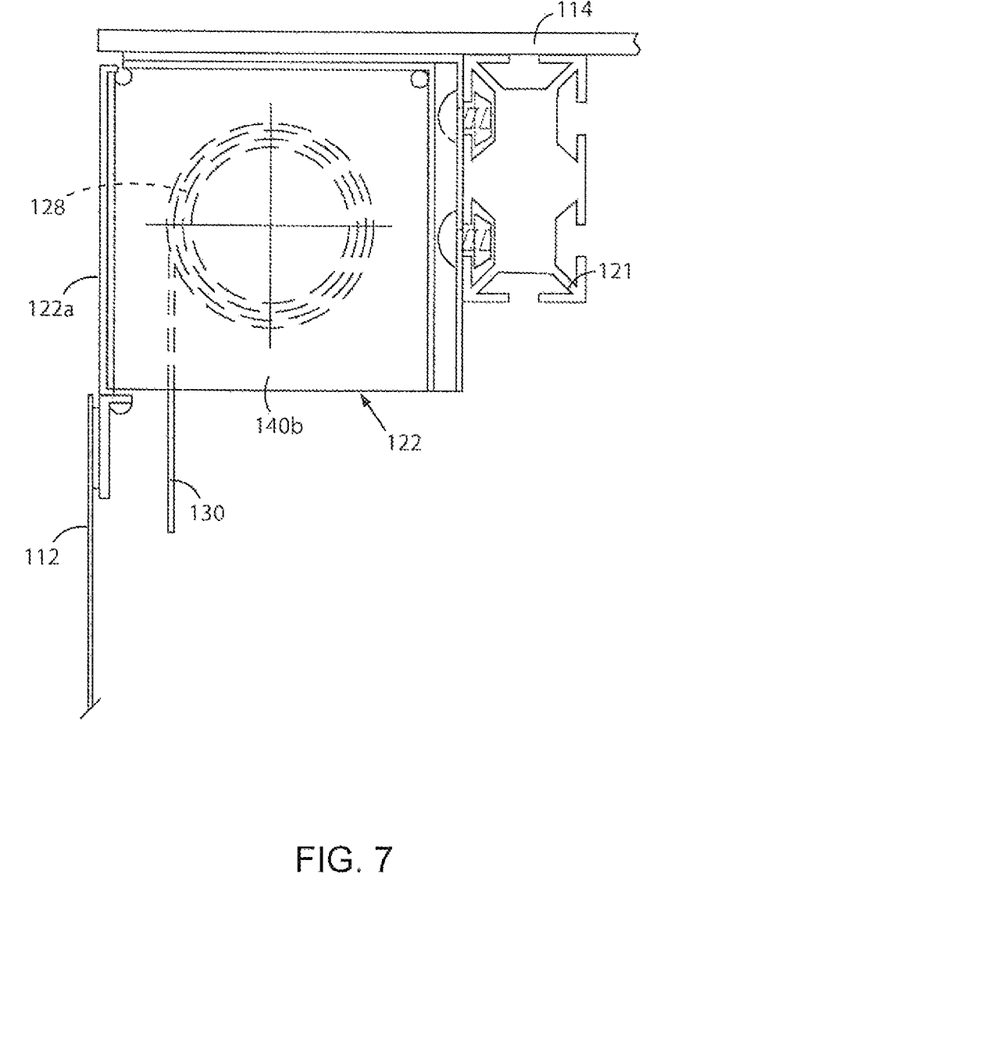
FIG. 7 is an end view of the inventive system, as seen in elevation along line B-B in FIG. 8.

The laser containment system 110 includes four elongated curtain pockets 120, 122, 124, 126 (see FIG. 5) each of which can be formed from one or more metal sheets to have a generally U-shaped cross section. As seen in FIGS. 6 and 7, the curtain pockets are preferably mounted beneath the platform 114 so that the outside walls of the pockets are substantially flush with the perimeter of the platform 114, with the open sides of the pockets facing downward. Each pocket is secured beneath the platform 114 by, for example, fastening an inside wall of the pocket to a side of an elongated "T-slot" frame member that projects beneath the platform 114, and runs parallel to the side of the platform along which the pocket is secured. See FIG. 6, which shows an inside wall 120a of pocket 120 fixed to frame member 121 beneath the platform 114.

Figure 8:
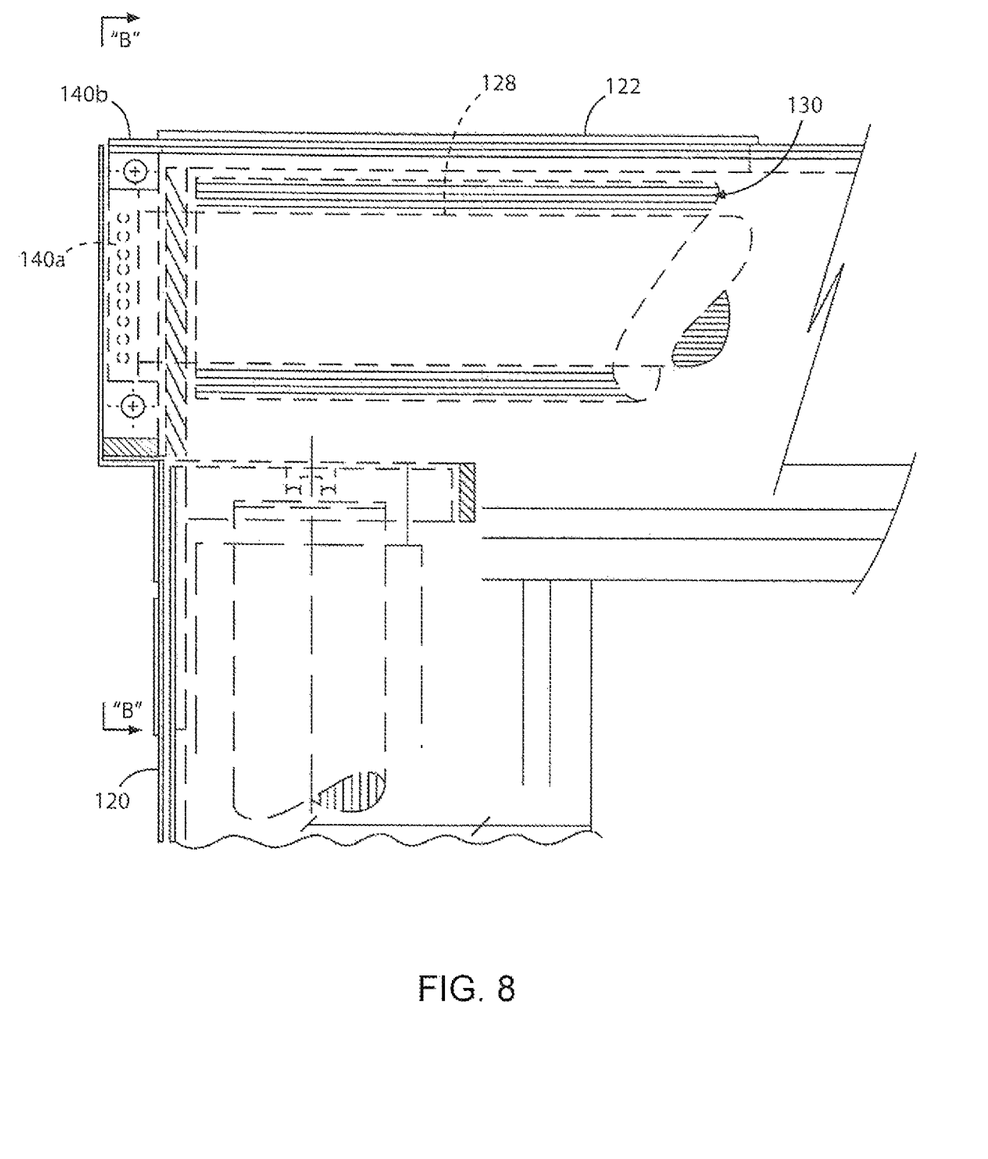
FIG. 8 is a top plan view of adjoining curtain pockets at the front corner of the inventive system shown in FIGS. 4 and 5.
Figure 9:
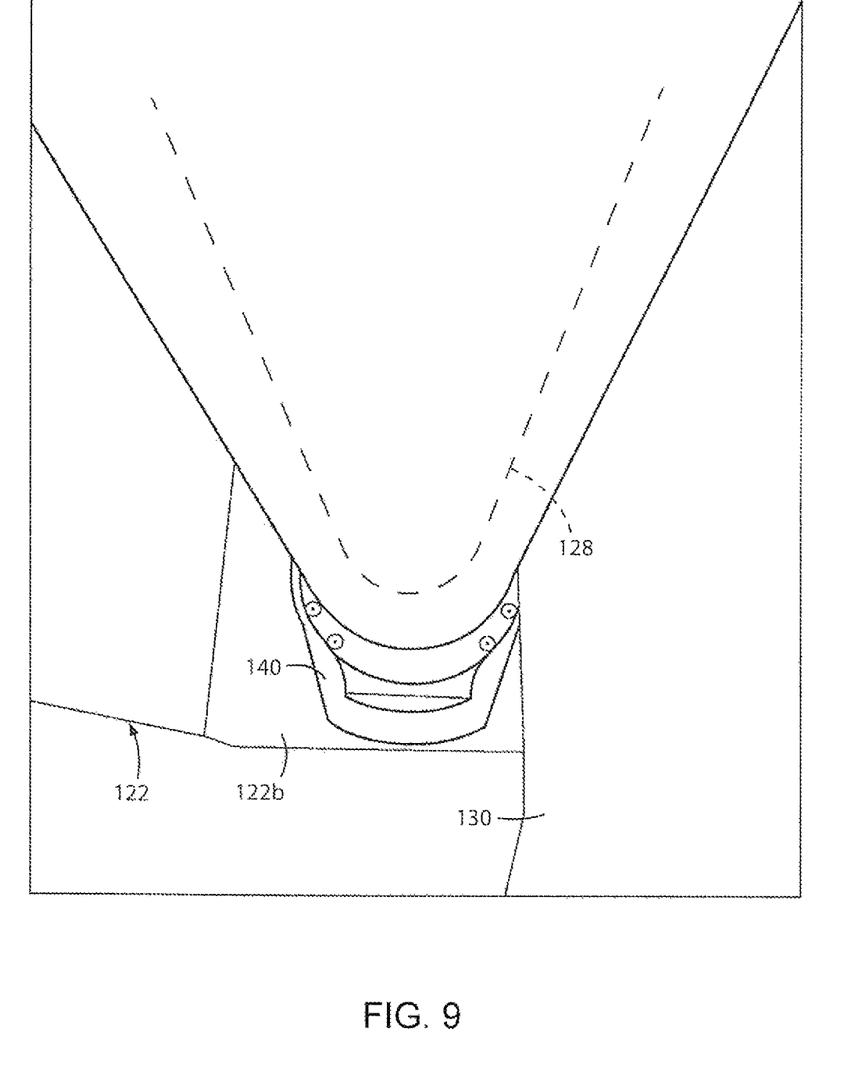
FIG. 9 is a perspective view in the axial direction of a roller mounted inside a curtain pocket, according to the invention.

An elongated curtain tube or roller 128 (see FIGS. 7 to 9) is disposed inside of each pocket. Each roller 128 is supported for rotation about its axis between end walls inside the pocket, and a commercially available fabric laser curtain 130 is wound substantially over the full length of the roller. The curtains 130 are wound so that they unwind from the sides of the rollers that face the outside walls of the pockets. See, e.g., FIG. 7 wherein the curtain 130 unwinds from the side of the roller 128 that faces the outside wall 122a of pocket 122.

A clutch 140 is supported on an end wall of each curtain pocket for engaging a corresponding end of the roller 128 mounted inside the pocket. See, e.g., FIG. 9 which shows the inside of pocket 122 as seen from below, including a roller 128 and a clutch 140 on pocket end wall 122b, wherein the clutch is axially engaged with the far end of the roller 128 as viewed in the drawing. The clutches 140 operate in a known manner to turn the rollers and thus lower or raise the curtains 130 through the open bottoms of the curtain pockets.

Each clutch 140 has an associated pulley 140a disposed outside the end wall of the pocket on which the clutch is supported. See FIG. 8. The circumference of each pulley 140a is formed to be engaged by a bead chain 150 that hangs down from the pulley by a determined length for access below. Each clutch pulley 140a is protectively enclosed by a cover 140b that extends approximately one inch from the end wall of the corresponding pocket. See FIGS. 3 and 8. The bottom of each cover 140b is open for clear passage of the pulley chain 150.

As noted above and shown in FIGS. 6 and 7, each of the four curtain pockets 120 to 126 may be fastened to conventional T-slot framing 121 fixed on the bottom surface of the platform 114, using T-slot nuts and bolts. Also, the tops of the corner protection pieces 112 may be removably fastened to the outside wall of each pocket where the pockets adjoin one another, to ensure adequate shielding is provided at the corners of the table when the curtains 130 are lowered. See FIGS. 3 and 7.

The curtains are sized and the curtain pockets are located according to the size of the table to be placed on the floor below the system 110, with a certain overhead. For example, for a table whose top measures 60"×48", an overhead of 4" may be added to determine the width of the corresponding curtains and the length and position of the pockets. Each curtain should descend preferably not more than about 1" to 3" away from a corresponding side of the table to allow for cables, hoses, and/or other services to be routed to and from the table.

In use, a researcher will typically need access to equipment on the top of the table from all four sides. Thus, when setting up an experiment on the table, all four curtains 130 should be wound upward. See FIGS. 3 and 4. When an experiment is ready to run, the curtains are drawn down around the sides of the table by operating the chains 150 from positions that are outside the curtains when drawn. The researcher then starts the experiment from a remote location. It will therefore be appreciated that the researcher no longer needs to disturb the curtains 130 or any of the corner protection pieces 112 in order to access the curtain chains 150 which hang outside of the curtains 130 when lowered.

The inventive system 110 is scalable. It can be manufactured with any width, depth, or height, the dimensions being restricted only by the maximum allowable deflection of the curtain rollers 128 used in the application. The system may also be motorized in a known manner, with electronics concealed in each pocket. It will also be appreciated that the system 110 may be modified to enable the curtain pockets 120 to 126 and the overhead platform to support piping and conduits for services such as gases, fluids, and lighting as a complete turn key kit for laboratory tables, with the end user having an ability to tailor the system as desired.

As result;

1. Because the chains for raising and lowering the curtains are operated from outside the protected field of the system, the number of times the protected field needs to be entered, the potential for injury to person and damage to property, and the wear and tear on the curtain fabric, are all reduced.

2. The corner protection pieces or flaps for covering any gaps between the side edges of the curtains at the table corners, can remain stationary and be installed permanently to ensure no laser light will exit from a corner of the table.

3. The inventive system can be suspended from the bottom or the side of a support platform that is hung over the table and used to route electrical wiring and other services to the table for experimentation.

4. The system is clean, functional, scalable, has an aesthetically pleasing appearance, and occupies less floor space so that more lines of sight are left open across a laboratory facility where the system is installed.

5. By installing each pocket with its open side facing downward, and unwinding the curtains from the sides of the rollers that face the outside walls of the pockets, the system will have a smaller overhead footprint than prior systems.

While the foregoing represents preferred embodiments of the present invention, it will be understood by persons skilled in the art that various changes, modifications, and additions can be made without departing from the spirit and scope of the invention. and that the invention includes all such changes, modifications, and additions as are within the bounds of the following claims.

I claim:

1. A laser curtain containment system, comprising:
a rectangular platform or track constructed and arranged to be suspended above a table on which a source of laser light is to be activated;
four elongated curtain pockets each of which has an outside wall, an inside wall, and opposite axial end walls, wherein each curtain pocket has a generally U-shaped cross section, and each pocket is constructed and arranged for mounting beneath a corresponding side of the rectangular platform or track so that an open side of each pocket faces downward toward a corresponding side of the table;
an elongated curtain roller of a certain length mounted for rotation between the axial end walls inside each one of the curtain pockets;
a laser curtain wound on the curtain roller inside each one of the curtain pockets, wherein each curtain is wide enough to extend over substantially the entire length of the roller between the axial end walls of the corresponding curtain pocket, and each curtain has sufficient length to be lowered from each pocket past a corresponding side of the table when each curtain is unwound;
a clutch supported on one of the axial end walls of each curtain pocket for operatively engaging an end of the curtain roller inside each pocket to lower or raise the curtain wound on each roller, wherein the clutch has an associated pulley disposed outside the axial end wall of each pocket on which the clutch is supported;
a protective cover disposed over the pulley outside the axial end wall of each curtain pocket on which the clutch is supported, wherein the cover has an open bottom end;
a chain for engaging a circumference of the pulley, wherein the chain passes clearly through the open bottom end of the protective cover; and the curtain pockets are mounted beneath the rectangular platform or track to adjoin one another at axial ends of each pocket, so that the chains that engage the pulleys of the curtain pockets are disposed for access outside the axial end walls of the pockets and safely outside of a protected field contained by the curtains when lowered about the table on which a source of laser light is to be activated.

2. A laser curtain containment system according to claim 1, wherein the platform or track comprises T-slot framing.

3. A laser curtain containment system according to claim 1, wherein the curtain pockets and the platform or track of the system are constructed and arranged to support conduits for one or more services associated with a laboratory table to be placed below the platform or track.

4. A laser curtain containment system according to claim 1, wherein the curtain pockets are positioned on the platform or track so that each curtain descends from the associated pocket by not more than three inches away from a corresponding side of the table.

5. A laser curtain containment system according to claim 1, wherein each curtain is arranged to unwind from a side of its associated curtain roller which faces the outside wall of each pocket in which the roller is mounted.

6. A laser curtain containment system according to claim 1, wherein the protective cover extends axially approximately one inch from the axial end wall of each corresponding pocket.

7. A laser curtain containment system according to claim 1, wherein the outside walls of the pockets are substantially flush with a perimeter of the platform.

8. A laser curtain containment system according to claim 1, including elongated corner absorbing pieces fastened to the outside walls of the curtain pockets at the axial ends of the pockets, for ensuring adequate shielding is provided at the corners of the table when the laser curtains are lowered past the sides of the table.

* * * * *